(12) United States Patent
Villa

(10) Patent No.: US 6,174,846 B1
(45) Date of Patent: Jan. 16, 2001

(54) LIQUID COMPOSITION WITH ENHANCED LOW TEMPERATURE STABILITY

(75) Inventor: Virgilio Villa, Bergenfield, NJ (US)

(73) Assignee: Lever Brothers Company, a division of Conopco, Inc., New York, NY (US)

(*) Notice: Under 35 U.S.C. 154(b), the term of this patent shall be extended for 0 days.

(21) Appl. No.: 08/993,497

(22) Filed: Dec. 18, 1997

(51) Int. Cl.$^7$ ............... C11D 1/37; C11D 1/83; C11D 3/37

(52) U.S. Cl. ............ 510/159; 510/130; 510/427; 510/430; 510/437; 510/477; 510/481; 510/488

(58) Field of Search .................. 106/271, 285; 424/59; 510/139, 151, 152, 155, 396, 537, 130, 159, 427, 430, 437, 477, 481, 488; 514/844, 938

(56) References Cited

U.S. PATENT DOCUMENTS

| | | | |
|---|---|---|---|
| 3,957,970 | * 5/1976 | Korkis | 424/70 |
| 5,683,683 | * 11/1997 | Scafidi | 424/70.19 |
| 5,720,961 | * 2/1998 | Fowler et al. | 424/401 |
| 5,736,125 | * 4/1998 | Morawsky et al. | 424/59 |
| 5,763,332 | * 6/1998 | Gordon et al. | 424/84 |
| 5,792,739 | * 8/1998 | He et al. | 510/422 |

FOREIGN PATENT DOCUMENTS

| | | |
|---|---|---|
| 94/01084 | 1/1994 | (WO). |
| 94/17166 | 8/1994 | (WO). |
| 96/02229 | 2/1996 | (WO). |
| 97/05857 | 2/1997 | (WO). |
| 97/29736 | 8/1997 | (WO). |
| 98/13022 | 4/1998 | (WO). |

* cited by examiner

Primary Examiner—Yogendra Gupta
Assistant Examiner—Gregory E. Webb
(74) Attorney, Agent, or Firm—Ronald A. Koatz

(57) ABSTRACT

The invention relates to liquid cleansing compositions in lamellar phase. Use of minimum amounts of defined polymeric hydrophilic emulsifier in combination with a lamellar phase inducing structurant has been found to enhance both initial viscosity and free thaw (low temperature) viscosity/stability.

7 Claims, 3 Drawing Sheets

INCI Name: PEG-30 Dipolyhydroxystearate
(Trade Name: Arlacel P135 ex-ICI)

SCHEMATIC STRUCTURE

Where the hydrophilic group, n, can vary from 2 to 60 and the hydrophobic group (hydroxystearate) can vary from from 1 to 50

LIQUID COMPOSITION WITH ENHANCED LOW TEMPERATURE STABILITY

BACKGROUND

1. Field of the Invention

The present invention relates to liquid cleansing compositions of the type typically used in skin cleansing or shower gel compositions which compositions are lamellar phase compositions. Such lamellar compositions are characterized by high zero shear viscosity (good for suspending) while simultaneously being very shear thinning such that they readily dispense in pouring.

2. Background

The rheological behavior of all surfactant solutions, including liquid cleansing solutions, is strongly dependent on the microstructure, i.e., the shape and concentration of micelles or other self-assembled structures in solution.

When there is sufficient surfactant to form micelles (concentrations above the critical micelle concentration or CMC), for example, spherical, cylindrical (rod-like) or discoidal micelles may form. As surfactant concentration increases, ordered liquid crystalline phases such as lamellar phase, hexagonal phase or cubic phase may form. The lamellar phase, for example, consists of alternating surfactant bilayers and water layers. These layers are not generally flat but fold to form submicron spherical onion like structures called vesicles or liposomes. The hexagonal phase, on the other hand, consists of long cylindrical micelles arranged in a hexagonal lattice. In general, the microstructure of most personal care products consist of either spherical micelles; rod micelles; or a lamellar dispersion.

As noted above, micelles may be spherical or rod-like. Formulations having spherical micelles tend to have a low viscosity and exhibit newtonian shear behavior (i.e., viscosity stays constant as a function of shear rate; thus, if easy pouring of product is desired, the solution is less viscous and, as a consequence, it doesn't suspend as well). In these systems, the viscosity increases linearly with surfactant concentration.

Rod micellar solutions are more viscous because movement of the longer micelles is restricted. At a critical shear rate, the micelles align and the solution becomes shear thinning. Addition of salts increases the size of the rod micelles thereof increasing zero shear viscosity (i.e., viscosity when sitting in bottle) which helps suspend particles but also increases critical shear rate (point at which product becomes shear thinning; higher critical shear rates means product is more difficult to pour).

Lamellar dispersions differ from both spherical and rod-like micelles because they can have high zero shear viscosity (because of the close packed arrangement of constituent lamellar droplets), yet these solutions are very shear thinning (readily dispense on pouring). That is, the solutions can become thinner than rod micellar solutions at moderate shear rates.

In formulating liquid cleansing compositions, therefore, there is the choice of using rod-micellar solutions (whose zero shear viscosity, e.g., suspending ability, is not very good and/or are not very shear thinning); or lamellar dispersions (with higher zero shear viscosity, e.g. better suspending, and yet are very shear thinning).

To form such lamellar compositions, however, some compromises have to be made. First, generally higher amounts of surfactant are required to form the lamellar phase. Thus, it is often needed to add auxiliary surfactants and/or salts which are neither desirable nor needed. Second, only certain surfactants will form this phase and, therefore, the choice of surfactants is restricted.

In short, lamellar compositions are generally more desirable (especially for suspending emollient and for providing consumer aesthetics), but more expensive in that they generally require more surfactant and are more restricted in the range of surfactants that can be used.

When rod-micellar solutions are used, they also often require the use of external structurants to enhance viscosity and to suspend particles (again, because they have lower zero shear viscosity than lamellar phase solutions). For this, carbomers and clays are often used. At higher shear rates (as in product dispensing, application of product to body, or rubbing with hands), since the rod-micellar solutions are less shear thinning, the viscosity of the solution stays high and the product can be stringy and thick. Lamellar dispersion based products, having higher zero shear viscosity, can more readily suspend emollients and are typically more creamy. Again, however, they are generally more expensive to make (e.g., they are restricted as to which surfactants can be used and often require greater concentration of surfactants).

In general, lamellar phase compositions are easy to identify by their characteristic focal conic shape and oily streak texture while hexagonel phase exhibits angular fan-like texture. In contrast, micellar phases are optically isotropic.

In should be understood that lamellar phases may be formed in a wide variety of surfactant systems using a wide variety of lamellar phase "inducers" as described, for example, in applicants copending application, U.S. Ser. No. 08/789,726 to Puvvada et al. Generally, the transition from micelle to lamellar phase are functions of effective average area of headgroup of the surfactant, the length of the extended tail, and the volume of tail. Using branched surfactants or surfactants with smaller headgroups or bulky tails are all effective ways of inducing transitions from rod micellar to lamellar.

One way of characterizing lamellar dispersions include measuring viscosity at low shear rate (using for example a Stress Rheometer) when additional inducer (e.g., oleic acid or isostearic acid) is used. At higher amounts of inducer, the low shear viscosity will significantly increase.

Another way of measuring lamellar dispersions is using freeze fracture electron microscopy. Micrographs generally will show lamellar microstructure and close packed organization of the lamellar droplets (generally in size range of about 2 microns).

One problem with certain lamellar phase compositions is that they tend to lose their lamellar stability in colder temperatures (e.g., 0 to 45° F.). While not wishing to be bound by theory, this may be because, in cold conditions, the oil droplets become less flexible and the spherical structure characterizing the lamellar interaction breaks into lamellar sheets instead.

BRIEF DESCRIPTION OF THE INVENTION

Unexpectedly, applicants have now found that certain polymeric emulsifiers, particularly hydrophilic groups modified on one or both ends, preferably both ends, by polyhydroxy fatty acid ester hydrophobic chains (e.g., dipolyhydroxystearate), can be used at small levels to enhance both initial viscosity and low temperature viscosity, thereby providing much more stable compositions.

More specifically, the invention comprises a liquid cleansing composition comprising:

(a) 5% to 50% by wt. of a surfactant system comprising:
  (i) at least one anionic surfactant or a mixture of anionic surfactants (e.g., 0.5 to 25% by wt.); and
  (ii) preferably an amphoteric and/or zwitterionic surfactant (e.g., betaine) or mixtures thereof (e.g., 0.1 to 25% by wt.);
(b) 0.1% to 15% by wt., preferably 1% to 10% by wt. of a lamellar phase inducing structurant selected from the group consisting of:
  (i) $C_8$ to $C_{24}$ unsaturated and/or branched liquid fatty acid or ester thereof;
  (ii) $C_8$ to $C_{24}$ unsaturated and/or branched liquid alcohol or ether thereof; and
  (iii) $C_5$ to $C_9$ saturated fatty acids;
    wherein said structurant has a melting point below about 25° C.;
(c) 0.1% to 5%, preferably 0.2% to 3%, more preferably 0.25% to 2% by wt. of a polymeric hydrophilic emulsifier modified on one or both ends, preferably both, with hydrophobic polyhydroxy fatty acid ester chains, (e.g., mono or dipolyhydroxy, $C_8$–$C_{24}$ fatty acid esters, particularly dipolyhydroxy stearate)
wherein said compositions have initial viscosity of greater than, 40,000 cps measured at 0.5 RPM using T-bar spindle A, preferably greater than 75,000 cps, more preferably from about 90,000 to about 150,000 cps, and freeze thaw viscosity (measured after at least one cycle, preferably at least 2 cycles, most preferably at 3 cycles of 15° F. to room temperature freeze thaw cycles) at greater than about 40,000 cps, preferably greater than 50,000 (again measured at 0.5 RPM using T-bar spindle A). Ideally, there should be no change in viscosity from initial viscosity although this of course is not always possible.

DETAILED DESCRIPTION OF THE INVENTION

Figure 1:
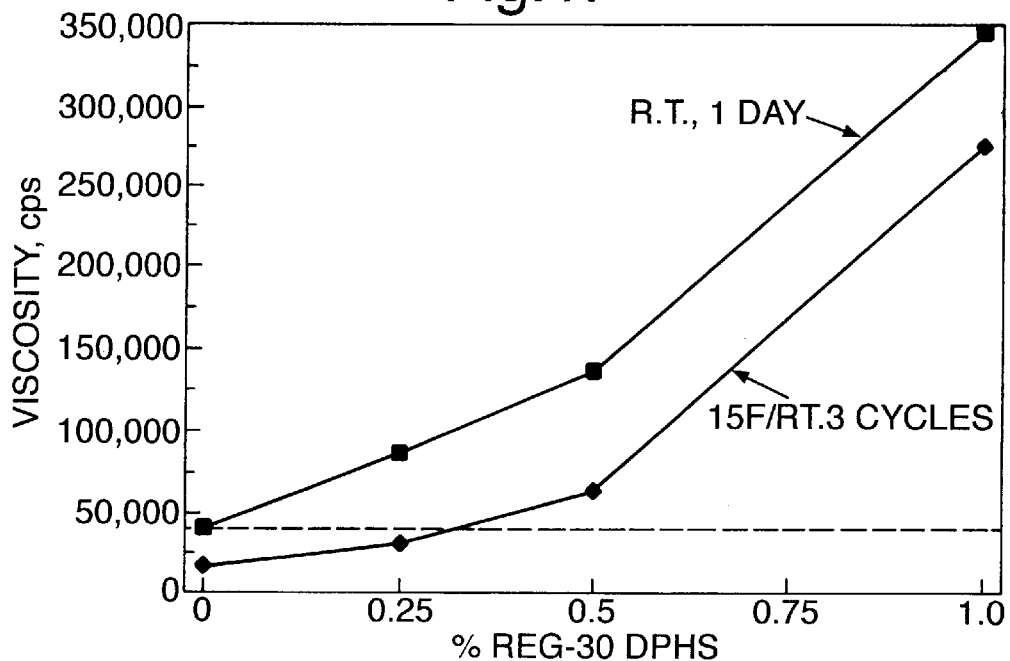
FIG. 1 shows effect of polymeric hydrophilic emulsifier of invention when used in combination with lamellar phase inducing structurant. The emulsifier enhances both initial and freeze-thaw viscosity compared to use of structurant with no emulsifier.

The present invention relates to liquid cleansing compositions, particularly lamellar structured liquid cleansing compositions comprising:
  (a) 5% to 50% by wt. of a surfactant system comprising one or more anionic surfactants and preferably further comprising an amphoteric and/or zwitterionic surfactant or mixtures thereof;
  (b) 1% to 15% by wt., preferably 1 to 10% by wt. of a lamellar phase inducing structurant which can be selected form the group consisting of:
    (i) $C_8$ to $C_{24}$ unsaturated and/or branched liquid fatty acid or ester thereof;
    (ii) $C_8$ to $C_{24}$ unsaturated and/or branched liquid alcohol or ether thereof; and
    (iii) $C_5$ to $C_9$ saturated fatty acids;
      wherein said structurant has a melting point below about 25° C.;
  (c) 0.1% to 5% of a polymeric hydrophilic emulsifier modified on one or both ends, preferably both with hydrophobic polyhydroxy fatty acid ester chains, (e.g., mono or dipolyhydroxy, $C_8$–$C_{24}$ fatty acid esters, such as, for example dipolyhydroxystearate);
    wherein said composition has initial viscosity of greater than 40,000 cps, preferably 90,000 to 130,000 cps; and freeze thaw viscosity of greater than 40,000 cps, preferably greater than 50,000 cps, wherein viscosity is measured at 0.5 RPM using T-bar spindle A.

Surfactants

The surfactant system of the subject invention comprises 5 to 50% by weight, preferably 10 to 40% by wt. of the composition and comprises:
  (a) one or more anionic surfactants;
  (b) amphoteric and/or zwitterionic surfactant; and
  (c) optional nonionic surfactant The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

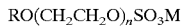
$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

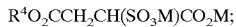
$$R^4O_2CCH_2CH(SO_3M)CO_2M;$$

amido-MEA sulfosuccinates of the formula

$$R^4CONHCH_2CH_2O_2CCH_2CH(SO_3M)CO_2M$$

wherein $R^4$ ranges from $C_8$–$C_{22}$ alkyl and M is a solubilizing cation; amido-MIPA sulfosuccinates of formula

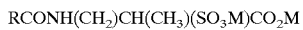
$$RCONH(CH_2)CH(CH_3)(SO_3M)CO_2M$$

where M is as defined above.

Also included are the alkoxylated citrate sulfosuccinates; and alkoxylated sulfosuccinates such as the following:

wherein n=1 to 20; and M is as defined above.

Sarcosinates are generally indicated by the formula RCON(CH$_3$)CH$_2$CO$_2$M, wherein R ranges from C$_8$ to C$_{20}$ alkyl and M is a solubilizing cation.

Taurates are generally identified by formula

wherein R$^2$ ranges from C$_8$–C$_{20}$ alkyl, R$^3$ ranges from C$_1$–C$_4$ alkyl and M is a solubilizing cation.

Another class of anionics are carboxylates such as follows:

wherein R is C$_8$ to C$_{20}$ alkyl; n is 0 to 20; and M is as defined above.

Another carboxylate which can be used is amido alkyl polypeptide carboxylates such as, for example, Monteine LCQ$^{(R)}$ by Seppic.

Another surfactant which may be used are the C$_8$–C$_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

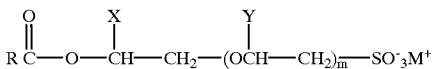

wherein R is an alkyl group having 8 to 18 carbons, m is an integer from 1 to 4, X and Y are hydrogen or an alkyl group having 1 to 4 carbons and M$^+$ is a monovalent cation such as, for example, sodium, potassium or ammonium.

In general the anionic component will comprise from about 1 to 20% by weight of the composition, preferably 2 to 15%, most preferably 5 to 12% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

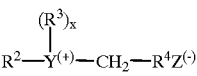

wherein R$^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; R$^3$ is an alkyl or monohydroxyalkyl group containing about 1 to about 3 carbon atoms; X is 1 when Y is a sulfur atom, and 2 when Y is a nitrogen or phosphorus atom; R$^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:

4-[N,N-di(2-hydroxyethyl)-N-octadecylammonio]-butane-1-carboxylate;

5-[S-3-hydroxypropyl-S-hexadecylsulfonio]-3-hydroxypentane-1-sulfate;

3-[P,P-diethyl-P-3,6,9-trioxatetradexocylphosphonio]-2-hydroxypropane-1-phosphate;

3-[N,N-dipropyl-N-3-dodecoxy-2-hydroxypropylammonio]-propane-1-phosphonate;

3-(N,N-dimethyl-N-hexadecylammonio)propane-1-sulfonate;

3-(N,N-dimethyl-N-hexadecylammonio)-2-hydroxypropane-1-sulfonate;

4-[N,N-di(2-hydroxyethyl)-N-(2-hydroxydodecyl)ammonio]-butane-1 -carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphonate; and

5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

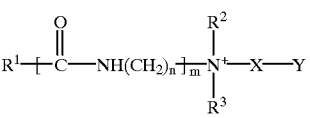

where R$^1$ is alkyl or alkenyl of 7 to 18 carbon atoms;

R$^2$ and R$^3$ are each independently alkyl, hydroxyalkyl or carboxyalkyl of 1 to 3 carbon atoms;

n is 2 to 4;

m is 0 to 1;

X is alkylene of 1 to 3 carbon atoms optionally substituted with hydroxyl, and

Y is —CO$_2$— or —SO$_3$—

Suitable amphoteric detergents within the above general formula include simple betaines of formula:

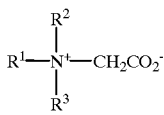

and amido betaines of formula:

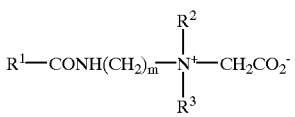

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

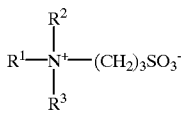

or

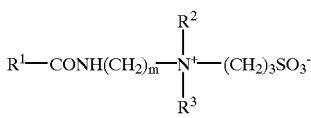

where m is 2 or 3, or variants of these in which —(CH$_2$)$_3$SO$^-_3$ is replaced by

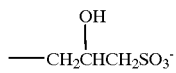

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, preferably 5% to 15% of the composition.

A preferred surfactant system of the invention comprises acyl isethionate in combination with betaine (e.g., cocoamido propylbetaine).

The surfactant system may optionally comprise a nonionic surfactant.

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(\text{glycosyl})_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

Nonionic comprises 0 to 10% by wt. of the composition.

Structurant

The present invention provides compositions utilizing about 0.1% to 15% by wt., preferably 1 to 10% by wt. of a structuring agent which works in the compositions to form a lamellar phase. Such lamellar phase is preferred because it enables the compositions to suspend particles more readily (e.g., emollient particles) while still maintaining good shear thinning properties. The lamellar phase also provides consumers with desired rheology ("heaping").

More particularly, where the composition is not lamellar structured and enhanced particle suspension/enhancing is desired, it is usually necessary to add external structurants such as carbomers (e.g., cross-linked polyacrylate such as Carbopol$^{(R)}$) and clays. However, these external structurants have poorer shear thinning properties that significantly reduce consumer acceptability.

The structurant is generally an unsaturated and/or branched long chain ($C_8$–$C_{24}$) liquid fatty acid or ester derivative thereof; and/or unsaturated and/or branched long chain liquid alcohol or ether derivatives thereof. It may also be a short chain saturated fatty acid such as capric acid or caprylic acid. While not wishing to be bound by theory, it is believed that the unsaturated part of the fatty acid of alcohol or the branched part of the fatty acid or alcohol acts to "disorder" the surfactant hydrophobic chains and induce formation of lamellar phase.

Examples of liquid fatty acids which may be used are oleic acid, isostearic acid, linoleic acid, linolenic acid, ricinoleic acid, elaidic acid, arichidonic acid, myristoleic acid and palmitoleic acid. Ester derivatives include propylene glycol isostearate, propylene glycol oleate, glyceryl isostearate, glyceryl oleate and polyglyceryl diisostearate.

Examples of alcohols include oleyl alcohol and isostearyl alcohol. Examples of ether derivatives include isosteareth or oleth carboxylic acid; or isosteareth or oleth alcohol.

The structuring agent may be defined as having melting point below about 25° C. centigrade.

Polymeric Hydrophilic Emulsifier

The key to the invention is the discovery that use of relatively small amounts of hydrophilic emulsifier modified at one or both ends, preferably both ends, with hydrophobic polyhydroxy fatty acid ester chains can remarkably enhance both initial viscosity/stability as well as freeze-thaw stability of the composition. Further, it does so without sacrificing lather production. Thus, as demonstrated in the examples, use of as little as 0.1%, preferably 0.25% of the emulsifier enhances viscosity of the composition relative to compositions which contain lamellar inducing structurant, but do not additionally contain the emulsifier.

The emulsifier may comprise a polyalkylene glycol backbone chain (e.g., $H(OCH_2CH_2)_nOH$) wherein n ranges from 2 to 60. Preferably, the polyalkylene glycol backbone unit is a $C_2$–$C_4$ alkylene glycol such as ethylene or propylene glycol.

One or both ends, preferably both, of the polyalkylene glycol backbone are modified with attached polyhydroxy fatty acid $C_8$ to $C_{24}$, preferably $C_{12}$ to $C_{20}$ esters such as, for example, polyhydroxystearate. If the group is stearate, for example, the hydrophobic group might be as follows:

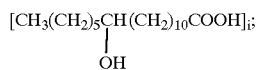

wherein i may vary from 1 to 50.

Figure 4:
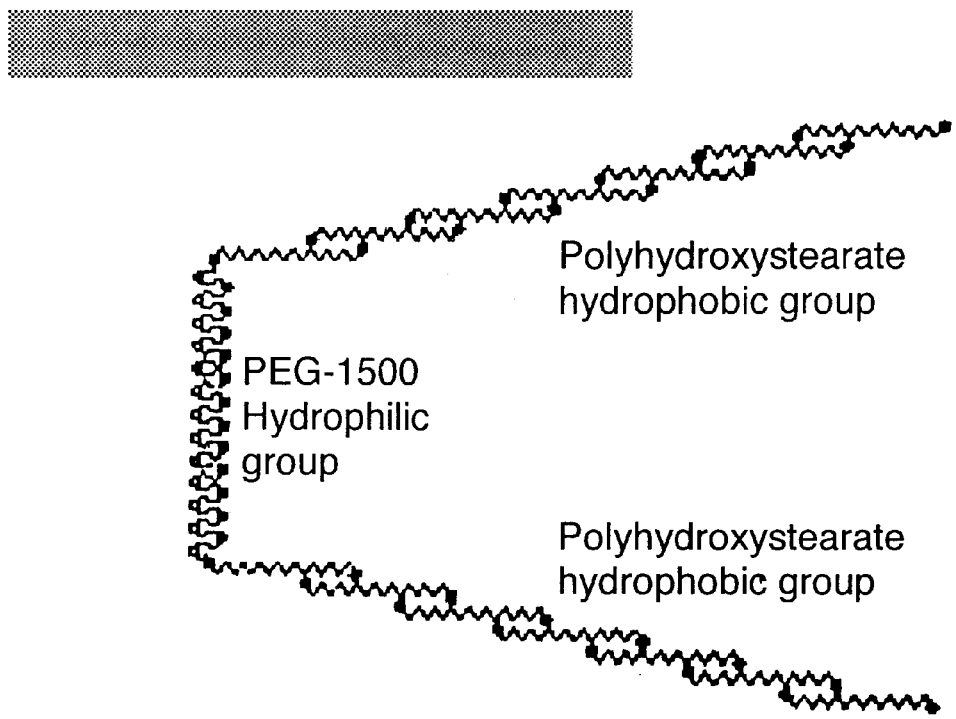
FIG. 4 is a schematic structure of a typical polymeric emulsifier, PEG-30 dipolyhydroxystearate.

FIG. 4 provides a schematic structure of a typical emulsifier which might be used having a polyalkylene glycol backbone as noted above and modified at both ends with hydrophobic groups (e.g., polyhydroxystearate) wherein number of groups at each end could vary from 1 to 50.

One example such an emulsifier which serves particularly well in the subject invention is PEG-30 dipolyhydroxystearate which is also known under the tradename Arlacel $P_{135}^{(R)}$ ex ICI. As noted, the number of repeating alkylene groups on the chain could vary from 2 to 60 and attached hydrophobic groups may be other polyhydroxy fatty acid esters, wherein number of groups at each end varies from 1 to 50.

A particularly good combination of the invention providing enhanced initial and freeze-thaw viscosity comprises use of isostearic acid in combination with PEG-30 dipolyhydroxystearate.

When isostearic acid alone, for example, is used as lamellar inducing structurant, the initial viscosity is about 40,000 cps, but when subjected to freeze-thaw tests when temperature is lowered (i.e., to be about 15° F.) and raised (i.e., to room temperature), the viscosity remains same or lower.

When even small amounts of emulsifier are used, however (e.g., 0.25%), both initial viscosity and freeze-thaw viscosity are enhanced.

Oil/Emollient

One of the principle benefits of the invention is the ability to suspend oil/emollient particles in a lamellar phase composition. The following oil/emollients may optionally be suspended in the compositions of the invention.

Various classes of oils are set forth below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acytylatelte lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include mineral oil, petrolatum, silicone oil such as dimethyl polysiloxane, lauryl and myristyl lactate.

It should be understood that where the emollient may also function as a structurant, it should not be doubly included such that, for example, if the structurant is 15% oleyl alcohol, no more than 5% oleyl alcohol as "emollient" would be added since the emollient (whether functioning as emollient or structurant) never comprises more than 20%, preferably no more than 15% of the composition.

The emollient/oil is generally used in an amount from about 1 to 20%, preferably 1 to 15% by wt. of the composition. Generally, it should comprise no more than 20% of the composition.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil$^{(R)}$ from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenylether (DP300); preservatives such as dimethyloldimethylhydantoin (Glydant XL 1000), parabens, sorbic acid etc.

The compositions may also comprise coconut acyl monoor diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330 -Polyquaternium 39; and Jaguar$^{(R)}$ type conditioners.

Polyethylene glycols which may be used include:

| Polyox | WSR-205 | PEG 14M, |
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm $^{(R)}$ (PEG modified glyceryl cocoate, palmate or tallowate) from Rewo Chemicals; Antil$^{(R)}$ 141 (from Goldschmidt).

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, walnut sheets and apricot seeds The invention will now be described in greater detail by way of the following non-limiting examples. The examples are for illustrative purposes only and not intended to limit the invention in any way.

All percentages in the specification and examples are intended to be by weight unless stated otherwise.

EXAMPLES

Tests relating to use of polymeric emulsifier in lamellar structured shower gel compositions where conducted in the following base compositions:

| Ingredient | Base<br>% by Wt. |
|---|---|
| Anionic Surfactant | 10–20% |
| Amphoteric Surfactant (e.g., betaine) | 1–15% |
| Oil/Emollient (e.g., Sunflower Seed Oil; Silicone; Petrolatum) | 0.1–10% |
| Opacifier/Colorant | 0–2% |
| Perfume/Preservative | 0–3% |
| Lamellar Inducing Structurant (e.g., Isostearic Acid) | 1–8% |
| Hydrophilic Emulsifier (e.g., Arlacel P135) | 0.5–5%, preferably about 1% |

Viscosity measurements were made in accordance with the following protocol:

Viscosity Measurement

Scope:

This method covers the measurement of the viscosity of the finished product. It is used to measure the degree of structuring of the product.

Apparatus:
  Brookfield RVT Viscometer with Helipath Accessory;
  Chuck, weight and closer assembly for T-bar attachment;
  T-bar Spindle A;
  Plastic cups diameter greater than 2.5 inches.

Procedure:
1. Verify that the viscometer and the helipath stand are level by referring to the bubble levels on the back of the instrument.
2. connect the chuck/closer/weight assembly to the Viscometer (Note the left-hand coupling threads).
3. Clean Spindle A with deionized water and pat dry with a Kimwipe sheet. Slide the spindle in the closer and tighten.
4. Set the rotational speed at 0.5 RPM. In case of a digital viscometer (DV) select the % mode and press autozero with the motor switch on.
5. Place the product in a plastic cup with inner diameter of greater than 2.5 inches. The height of the product in the cup should be at least 3 inches. The temperature of the product should be 25° C.
6. Lower the spindle into the product (~¼ inches). Set the adjustable stops of the helipath stand so that the spindle does not touch the bottom of the plastic cup or come out of the sample.
7. Start the viscometer and allow the dial to make one or two revolutions before turning on the Helipath stand. Note the dial reading as the helipath stand passes the middle of its downward traverse.
8. Multiply the dial dreading by a factor of 4,000 and report the viscosity reading in cps.

Example 1

Using the base noted above, applicants prepared compositions comprising base, oil, Arlacel P135 and isostearic acid as noted below and obtained viscosity results at both normal (room temperature) and accelerated conditions as follows:

| Example | A | 1 | 2 | B | 3 | C | 4 | D | 5 |
|---|---|---|---|---|---|---|---|---|---|
| Base | As noted | As noted | As noted | As noted | As noted | As noted | As noted | As noted | As noted |
| Oil | 5%<br>Dimethi-cone | 5%<br>Dimethi-cone | 5%<br>Dimethi-cone | 7.5%<br>Petrola-tum | 7.5%<br>Petrola-tum | 7.5%<br>Mineral Oil | 7.5%<br>Mineral Oil | 7.5%<br>Sunflower Seed Oil | 7.5%<br>Sunflower Seed Oil |
| Arlacel P135 | 0% | 0.5% | 0.25% | 0% | 1% | 0% | 1% | 0 | 0.5 |
| Isostearic Acid | 5% | 5% | 5% | 5% | 5% | 5% | 5% | 4.5% | 4.5% |
| Viscosity, cps | | | | | | | | | |
| Normal, Room Temperature | | | | | | | | | |
| Initial | 61,600 | 280,200 | 236,200 | 97,200 | 103,900 | 32,400 | 95,200 | 40,600 | 136,800 |
| 1 Day | 61,800 | 322,100 | 255,600 | 88,900 | 135,000 | 27,900 | 102,700 | 32,900 | 136,600 |
| 1 Week | | | | | | 22,800 | 85,600 | 31,100 | 137,100 |
| 2 Weeks | | | 260,100 | | 159,700 | | | | 139,800 |
| 4 Weeks | 61,300 | 301,900 | | | | | | | |
| Accelerated | | | | | | | | | |
| 15F/RT, 3 cycles | 29,700 | 100,100 | 90,800 | 38,300 | 145,900 | 24,200 | 118,200 | 16,200 | 63,200 |

As can be seen from the data, when 0% Arlacel P135 was used (Comparatives A, B, C and D), both initial viscosity and freeze-thaw viscosity were significantly lower compared to use of small amounts of Arlacel (A versus 1 & 2; B versus 3, C versus 4, and D versus 5 ).

As noted, this was true no matter which oil was used.

Example 2

Again using a composition noted above, applicants tested for both initial and low temperature viscosity enhancement in compositions comprising varying levels of active (PEG-30 dipolyhydroxystearate) and isostearic acid. Either levels of emulsifier or lamellar inducing structurant can be varied although preferably it is level of emulsifier which is varied to ensure foam volume is maintained.

As noted in FIG. 1, use of even low levels of dipolyhydroxystearate resulted in significant improvements in both initial and freeze-thaw viscosity compared to use of isostearic acid alone where viscosity remained low and certainly was not enhanced following freeze-thaw treatment.

It should be noted that 40,000 cps (seen in FIG. 1 as a dotted line) is minimum target for acceptable rheology and aesthetic pleasing according to the subject invention.

Example 3

Figure 2:
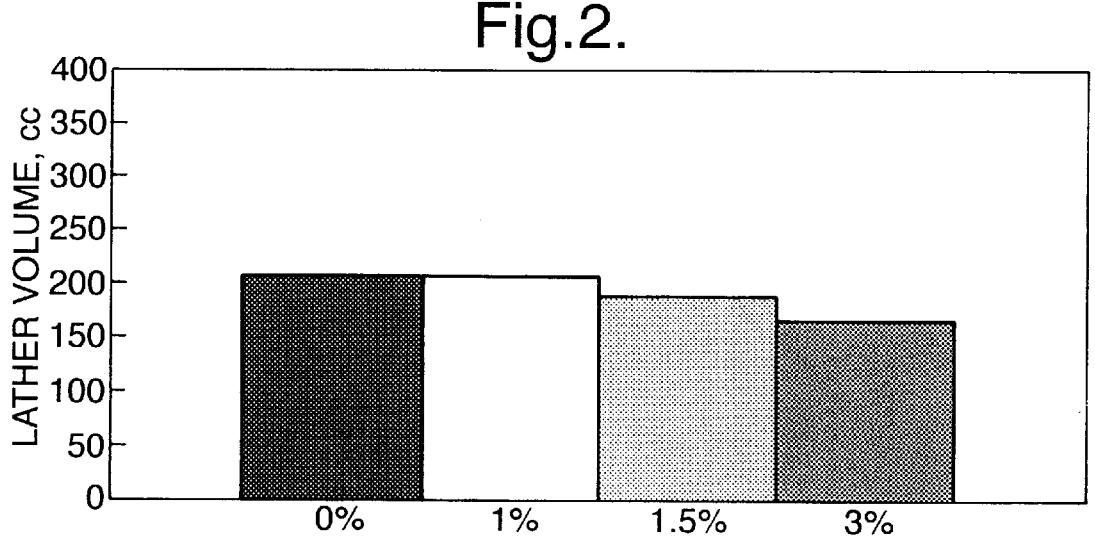
FIG. 2 shows that, for a given level of lamellar inducing structurant (e.g., isostearic acid at 5%), use of emulsifier (e.g., Arlacel P135) has no significant negative impact on lather production.

Applicants tested effect of isostearic acid versus Arlacel P135 as shown in FIG. 2.

This figure shows that, at given levels lamellar inducing structurant (5% isostearic acid), use of emulsifier has no significant negative effect on lather.

Example 4 (Comparative)

To show that Arlacel was providing significant effect, applicants tested known products that are lamellar structured for freeze-thaw stability after 3 cycles. Data is shown below.

| VISCOSITY PROFILE: COMPETITIVE PRODUCTS | | |
|---|---|---|
| | VISCOSITY, cps | |
| PRODUCTS | INITIAL (R.T.) | 15 F/R.T. (3 CYCLES) |
| OLAY REG (Sample 1) | 119,400 | 31,300 |
| OLAY REG (Sample 2) | 107,100 | 36,000 |
| OLAY REG (Sample 3) | 106,600 | 32,700 |
| OLAY REG (Sample 4) | — | 25,400 |
| OLAY REG (Sample 5) | 126,700 | 26,200 |
| OLAY SENS (Sample 1) | 130,700 | 21,600 |
| OLAY SENS (Sample 2) | 111,100 | 22,000 |
| IVORY MOISTURE CARE (Sample 1) | 141,300 | 49,400 |
| IVORY MOISTURE CARE (Sample 2) | 233,500 | 29,800 |

As clearly seen, in the absence of Arlacel P135, the viscosities were significantly lower than initial viscosity as well as below the 40,000 cps viscosity target required for the compositions of the subject invention (i.e., to provide good rheology and aesthetically pleasing properties).

Example 5

Figure 3A:
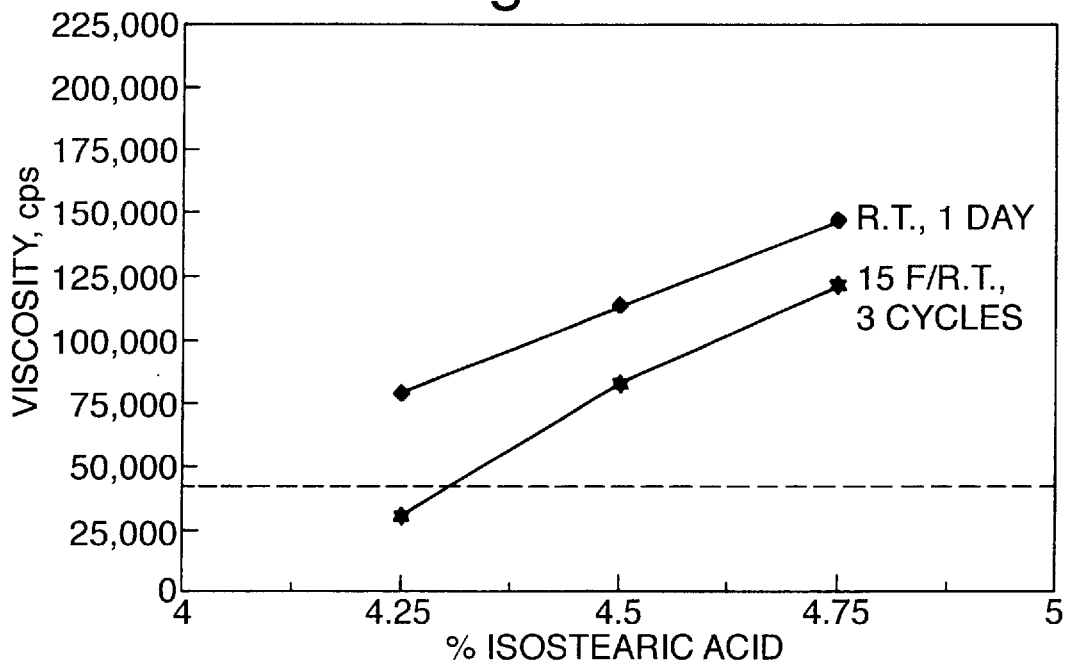
FIGS. 3A and 3B shows that, although it is possible to improve initial and freeze-thaw viscosity by increasing level of isostearic acid, for example, in combination with 0.5% Arlacel P135 (FIG. 3A), the additional isostearic acid added to constant small level of Arlacel P135 will negatively impact on lather volume (FIG. 3B). Therefore, to improve both stability without effecting lather volume, the focus should be on using emulsifier rather than increasing lamellar inducing structurant.
Figure 3B:
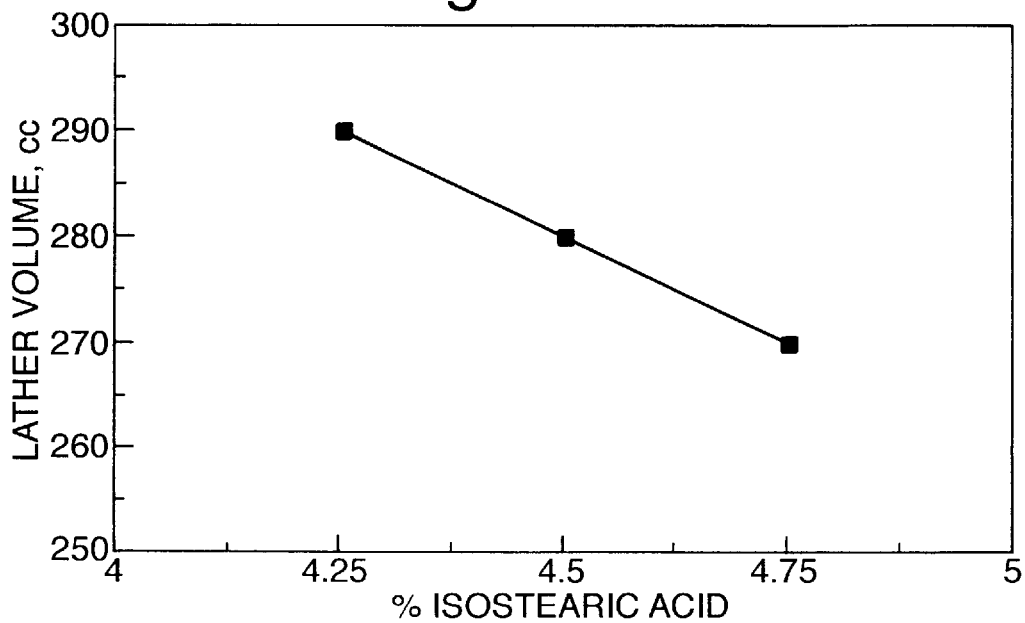

Although initial viscosity and freeze-thaw viscosity can be improved by addition of lamellar inducing structurant (e.g. isostearic acid), in combination with polyethylene glycol for example, (FIG. 3A), if it is added to a constant small level of emulsifier, lather volume is effected (FIG. 3B).

Thus, in preferred embodiments of invention, focus is on using more emulsifier rather than just increasing lamellar inducing structurant.

I claim:
1. Liquid cleansing composition comprising:
   (a) 5% to 50% by wt. of a surfactant system comprising:
      (i) 0.5 to 25% by wt. total composition of at least one anionic or mixture of anionic surfactants; and
      (ii) 0.1 to 25% by wt. total composition of a surfactant selected from the group consisting of amphoteric, zwitterionic or mixtures thereof;
   (b) 0.1% to 15% by wt. of a lamellar phase inducing structurant selected form the group consisting of:
      (i) $C_8$ to $C_{24}$ unsaturated and/or branched liquid fatty acid or ester thereof,
      (ii) $C_8$ to $C_{24}$ unsaturated and/or branched liquid alcohol or ether thereof; and
      (iii) $C_5$ to $C_9$ saturated fatty acids;
      wherein said structurant has a melting point below about 25° C.;
   (c) 0.1% to 5% by wt. of a polymeric hydrophilic emulsifier; wherein the composition has initial viscosity of greater than 40,000 cps, measured at 0.5 RPM using T-bar spindle A at temperature of about 25° C. and freeze-thaw viscosity of greater than about 40,000 cps also measured at 0.5 RPM using T-bar spindle A at temperature of about 25° C.;
      wherein said emulsifier is a polyalkylene glycol backbone chain $H(O(CH_2)_a)_nOH$;
      wherein a is 2–4 and n is 2 to 60 having from 4 to about 50, hydroxy $C_8$ to $C_{24}$ fatty acid groups attached to the backbone chain.

2. A composition according to claim 1, wherein anionic is acyl isethionate.

3. A composition according to claim 1, wherein (a)(ii) is an amphoteric surfactant which is betaine.

4. A composition according to claim 1, wherein the structurant is isostearic acid.

5. A composition according to claim 1, wherein the hydroxy $C_8$ to $C_{24}$ fatty acid group or groups attached to the backbone chain is hydroxystearic acid.

6. A composition according to claim 1, wherein initial viscosity is greater than 75,000 cps.

7. A composition according to claim 1, wherein initial viscosity is 90,000 to 135,000 cps.

* * * * *